United States Patent
Tregger et al.

(10) Patent No.: US 12,151,400 B2
(45) Date of Patent: Nov. 26, 2024

(54) WIDE SPEED RANGE CONCRETE MONITORING CALIBRATION

(71) Applicant: VERIFI LLC, Cambridge, MA (US)

(72) Inventors: Nathan A. Tregger, Northborough, MA (US); Mark F. Roberts, North Andover, MA (US); Kati Hazrati, Concord, MA (US); Greg A. Goldstein, Somerville, MA (US)

(73) Assignee: VERIFI LLC, Cambridge, MA (US)

( * ) Notice: Subject to any disclaimer, the term of this patent is extended or adjusted under 35 U.S.C. 154(b) by 53 days.

(21) Appl. No.: 18/140,304

(22) Filed: Apr. 27, 2023

(65) Prior Publication Data

US 2023/0256653 A1    Aug. 17, 2023

Related U.S. Application Data

(62) Division of application No. 15/781,645, filed as application No. PCT/US2015/064257 on Dec. 7, 2015, now Pat. No. 11,667,054.

(51) Int. Cl.
    *B28C 7/02*         (2006.01)
    *B28C 5/42*         (2006.01)
    (Continued)

(52) U.S. Cl.
    CPC .............. *B28C 5/422* (2013.01); *B28C 7/026* (2013.01); *B01F 2101/28* (2022.01); *G01N 2011/0053* (2013.01)

(58) Field of Classification Search
    CPC ..................................................... B28C 7/026
    (Continued)

(56) References Cited

U.S. PATENT DOCUMENTS

| | | |
|---|---|---|
| 5,713,663 A | 2/1998 | Zandberg et al. |
| 5,752,768 A | 5/1998 | Assh |

(Continued)

FOREIGN PATENT DOCUMENTS

| | | |
|---|---|---|
| CN | 102944670 A | 2/2013 |
| JP | 2010-249742 A | 11/2010 |

(Continued)

OTHER PUBLICATIONS

International Search Report and Written Opinion mailed Feb. 16, 2016 in corresponding PCT application No. PCT/US2015/064257.

(Continued)

*Primary Examiner* — David L Sorkin
(74) *Attorney, Agent, or Firm* — NIELDS, LEMACK & FRAME, LLC

(57) ABSTRACT

A method and system for concrete monitoring calibration using truck-mounted mixer drum jump speed data selectively assimilated from previous deliveries. In preferred embodiments, the invention surprisingly employs data obtained using different concrete mix designs, as well as jump speed data obtained from high speed mixing after the trucks arrive at the construction delivery site and before pouring the concrete into place at the site. The method involves measuring energy (E) in terms of pressure or force associated with mixing the concrete ("E1") at a first drum speed ("V1") and measuring energy (E2) after a speed jump of +/−2.5 RPM or more to a second drum speed (V2). Slump is calculated using low speed energy/speed/slump curve data, or pre-stored equation wherein slump(S) is derived as a function of slope of the line defined by E1, V1 and E2, V2 and intercept of the plotted relationship (at E axis where V is zero). The E/V/S relationship in the provided concrete is compared to at least two pre-stored data curves across drum speed ranges of 0.5 RPM-6 RPM and 6 RPM-20 RPM, to (Continued)

ascertain whether the provided concrete matches any of the stored curve data (i.e., previous concrete E/V/S profiles); and either activating the monitoring system for all drum speed ranges where a match is confirmed or allowing the monitoring system to calculate slump only at low drum speeds (below 6 RPM) and alerting a system user or operator that the system is only active for low speed monitoring.

8 Claims, 3 Drawing Sheets

(51) Int. Cl.
    *B01F 101/28*      (2022.01)
    *G01N 11/00*      (2006.01)

(58) Field of Classification Search
    USPC .............................................. 700/265; 366/8
    See application file for complete search history.

(56) References Cited

U.S. PATENT DOCUMENTS

| | | | |
|---|---|---|---|
| 6,042,258 | A | 3/2000 | Hines et al. |
| 6,484,079 | B2 | 11/2002 | Buckelew |
| 8,020,431 | B2 | 9/2011 | Cooley et al. |
| 8,118,473 | B2 | 2/2012 | Compton et al. |
| 8,311,678 | B2 | 11/2012 | Koehler et al. |
| 8,491,717 | B2 | 7/2013 | Koehler et al. |
| 8,727,604 | B2 | 5/2014 | Compton et al. |
| 8,746,954 | B2 | 6/2014 | Cooley et al. |
| 8,764,272 | B2 | 7/2014 | Hazrati et al. |
| 8,764,273 | B2 | 7/2014 | Koehler et al. |
| 8,818,561 | B2 | 8/2014 | Koehler et al. |
| 8,960,990 | B2 | 2/2015 | Koehler et al. |
| 8,989,905 | B2 | 3/2015 | Sostaric et al. |
| 11,667,054 | B2 | 6/2023 | Tregger et al. |
| 2007/0185636 | A1 | 8/2007 | Cooley et al. |
| 2010/0312438 | A1 | 12/2010 | Cooley et al. |
| 2011/0029134 | A1 | 2/2011 | Hazrati et al. |
| 2012/0004790 | A1 | 1/2012 | Cooley et al. |
| 2012/0016523 | A1 | 1/2012 | Koehler et al. |
| 2012/0020180 | A1 | 1/2012 | Koehler et al. |
| 2012/0204625 | A1 | 8/2012 | Beaupre et al. |
| 2014/0104972 | A1* | 4/2014 | Roberts ................. B28C 7/0454 700/265 |
| 2014/0107844 | A1 | 4/2014 | Koehler et al. |
| 2015/0051737 | A1 | 2/2015 | Berman |
| 2015/0142362 | A1 | 5/2015 | Jordan et al. |
| 2017/0361491 | A1 | 12/2017 | Datema et al. |
| 2020/0262105 | A1 | 8/2020 | Tregger et al. |

FOREIGN PATENT DOCUMENTS

| | | |
|---|---|---|
| KR | 2012-0004424 A | 1/2012 |
| WO | 2010/110814 | 9/2010 |
| WO | 2013/144528 | 10/2013 |
| WO | 2015/073825 | 5/2015 |
| WO | 2015/160610 | 10/2015 |

OTHER PUBLICATIONS

Korean communication, with English translation, dated Aug. 12, 2022 in corresponding Korean patent application No. 10-2018-7017633.

* cited by examiner

WIDE SPEED RANGE CONCRETE MONITORING CALIBRATION

This application is a divisional of U.S. patent application Ser. No. 15/781,645 filed Jun. 5, 2018, which is a 371 of PCT/US2015/064257 filed Dec. 7, 2015, the disclosures of which are incorporated herein by reference in their entireties.

FIELD OF THE INVENTION

The present invention relates to measurement of concrete, and, more particularly, to a method and system for wide speed range concrete monitoring calibration using truck-mounted drum jump speed data selectively assimilated from different previous concrete deliveries.

BACKGROUND OF THE INVENTION

In U.S. Pat. Nos. 8,020,431, 8,746,954, and 8,989,905 (assigned to Verifi LLC), Cooley et al. explained that when a concrete mix was rotated within a truck-mounted mixer drum at a stable (constant) speed, the slump of the concrete could be calculated by reference to an empirically generated "lookup table" that identified the slump value associated with the average hydraulic pressure required to rotate the concrete drum at the reference drum speed, e.g., 3 RPM. Hence, a slump value could be calculated, with respect to the reference drum speed, for each pressure value within a wide range of pressure readings in the lookup table. See U.S. Pat. No. 8,020,431, col. 11, lines 7-13.

However, while the relationship between pressure and drum speed is observed by Cooley et al. to be "approximately" linear when drum speed is about 3 RPM, it becomes pronouncedly "non-linear" at higher drum speeds, e.g., 10 RPM, which is higher than the reference speed of the lookup table. See U.S. Pat. No. 8,020,431, col. 11. ll. 14-17, 55-58.

While this does not present a serious issue for low speed mixing (e.g., 3 RPM) as typically occurs during transit from the batching plant, Cooley et al. noted that there were situations in which faster mixing speeds were used. They discuss at length, for example, the batch mixing which occurs immediately after loading of the mix components into the truck drum: when the truck moves to a "slump rack" where it performs higher speed mixing, then adjusts the load, then performs more high speed mixing, and then slows down the drum to travel speed and departs for the delivery site from the plant. See U.S. Pat. No. 8,020,431, col. 11. ll. 20-26.

Cooley et al. postulated that a compensation factor, called a calibrated rpm factor or "RPMF," could be assigned to each truck to support management of higher mixing rates and thereby avoid "manual" or empirical calibration of the truck at higher drum speeds. See U.S. Pat. No. 8,020,431, col. 11, ll. 14-17, 35-40. Their belief was that RPMF was different from truck to truck and based upon "a variety of reasons [which included] the buildup in the drum of the truck, fin shape, hydraulic efficiency variation, and others." See U.S. Pat. No. 8,020,431, col. 12, ll. 23-26.

As Cooley et al. desired to avoid the burdensome task of calibrating and re-calibrating the RPMF for each truck, they postulated a self-calibration process using a "theory of slump continuity" which was based on the premise that slump of the concrete mix remains the same during a sudden change in the drum speed:

" . . . The theory of slump continuity is that, over a short period of time, absent extraneous factors such as addition of water or mixture, slump remains relatively constant even if drum speed changes. Therefore the rpm compensation described above may be tested whenever there is a drum speed change, by comparing an observed change in average pressure caused by the drum speed change, to the predicted change in average pressure. If the predicted pressure change is erroneous, the rpm factor RMPF may be adjusted."

See U.S. Pat. No. 8,020,431, col. 11, lines 30-39.

The self calibration process based on the above slump continuity theory, as typified by drum speed changes that occur at batch plant mixing, was further described by Cooley et al. as follows:

"The self calibration proceeds as follows: when a drum speed change from a higher to a lower speed occurs, the average pressure at the higher speed (before the speed change) is used to compute a predicted pressure at 3 rpm, and the average pressure at the lower speed (after the speed change) is similarly used to compute a predicted pressure at 3 rpm, in each case using the process described above. If the predicted 3 rpm pressure derived from the higher speed is larger than the predicted 3 rpm pressure derived from the lower speed, this indicates that the RPMF overestimating the pressure increase [is] caused by speed reduction, and the RPMF is reduced so that the two predicted 3 rpm pressures are equal. If the predicted 3 rpm pressure derived from the lower speed is larger than the predicted 3 rpm pressure derived from the higher speed, this indicates that the RPMF is underestimating the pressure increase caused by speed reduction, and the RPMF is increased so that two predicted 3 rpm pressures are equal.

See U.S. Pat. No. 8,020,431, col. 12, lines 50-67.

The present inventors propose to follow the "theory of slump continuity" described by Cooley et al., but, on the other hand, they chart out a fundamentally different approach in resolving the inaccuracy of rheology monitoring which arises from the non-linear relationship between force or pressure and high drum speeds. "At higher drum speeds, the RPMF increases." observed Cooley et al . . . who believed that for "the purposes of slump calculation, the increase in the RPMF is handled in a piecewise linear fashion."

The present inventors believe that the arithmetic adjustment suggested by Cooley et al. ("at drum speeds from 6-10 rpm, the RPMF is doubled and above 10 RPM, the RPMF is quadrupled") does not resolve the "non-linearity" problem at higher mixing speeds because it only involved one mix design. The present inventors discovered that concrete mix design differences introduce greater variability and non-linearity within energy/slump/drum-speed curve data: this lack of curvilinear predictability is more pronounced at higher drum mixing speeds (~10 RPM), and most pronounced at the highest mixing speeds (16-20 RPM or more).

Until the present invention, it has remained the case that automated slump monitoring systems do not self-calibrate above the low speed mixing range (above 3-4 RPM) and that slump curves still need to be manually generated using standard slump cone measurements. In the higher ranges of drum rotation speeds, the viscosity of concrete mixes can be profoundly affected by mix constituents and proportions, and, in turn, these factors can cause variable effects on the pressure or force associated with moving the concrete at the higher drum rotation speeds (See e.g., Application of Rheological Measurements to Practical Control of Concrete in Rheology of Fresh Cement and Concrete, ed. P.F.G. Banfill, British Society of Rheology, Tattersall, 1991: See also Testing and Modeling of Fresh Concrete Rheology, Ferraris, de Larrard: NIST (Report NISTIR 6094) 1998.

Consequently, without taking the time and expending the labor to calibrate the slump monitoring system across the entire range of drum speeds, e.g., from 0.5 to 20 RPM, in ladder-like fashion, commercial monitoring systems are only used in low speed mixing applications where the speed range is typically 2-4 or 2-5 RPM at best.

The ability to measure slump only at low speeds is disadvantageous for many reasons. First, measuring at low speed is time-consuming, because often one or more revolutions of the drum are required before concrete mixes stabilize. This operation takes several minutes. As the ready-mix industry is essentially a shipping industry, wasted time is costly. Time can also be wasted during fluid additions used for adjusting slump.

Second, while the concrete can only be accurately monitored when the drum speed is below a certain RPM level, various concrete mix plants sometimes impose different mixing speed regimes for their particular mix designs, and these do not always coincide with optimum drum speeds required by the slump monitoring system.

Third, current typical industry practices prolong the delivery process whereby the slump monitoring system is only calibrated accurately for low speeds (e.g., 0.5-5 RPM). However, the present inventors are mindful of the industry practices described by ASTM C94, which requires that, if fluid additions are made to the concrete before pouring at the construction site, the speed of the mixing drum must be raised to high speed to ensure homogeneity (completeness of mixing) of the delivered concrete. If 30 rotations are required at high speed, during which an automated slump monitoring system cannot provide an accurate reading because it is not calibrated for that particular mix design at high speed, then the drum speed must be lowered after 30 rotations to a lower speed for monitoring purposes; and, if the monitored slump does not match a target slump (i.e., the slump value specified for the pouring event) and a fluid must be added to adjust the concrete mix to the desired slump, the drum speed must be increased again to high RPM until a homogenous mixture is attained before the mixer drum can again be slowed down so that it returns to the lower speed at which the system was calibrated, whereby accurate slump monitoring can be better achieved. All this, according to ASTM C94, must be done within 15 minutes from the first addition; and, hence, repeated additions may not necessarily be done within this time frame.

Hence, slump monitoring systems that are calibrated only for low speed measurement require that mixer drum speed be dropped to below 5 RPM, and, more typically, to 2-3 RPM, after which more adjustments at higher drum speeds are often necessary.

The present inventors believe that there has been a long felt need for an automated calibration process that will permit accurate adjustments to be made to the rheology (e.g., slump, slump flow, yield stress, etc.) of the current concrete load using such monitoring systems, a process that will ensure accurate and efficient monitoring that will allow for high speed mixing monitoring. This would be beneficial for industrial use of concrete delivery truck-mounted mixer drums.

SUMMARY OF THE INVENTION

In surmounting the disadvantages of prior art approaches, the present invention provides a method and system for wide speed range concrete monitoring calibration using truck-mounted mixer drum "jump speed" curve data that is selectively assimilated from different previous concrete deliveries. Surprisingly, the present invention permits the use of jump speed data obtained from prior concrete deliveries involving different concrete mix designs.

The terms "curve data" or "data curves" are used herein to refer to data comprising energy associated with rotating a concrete mix, in terms of hydraulic pressure required for rotating the concrete or force exerted by concrete moving against a probe (e.g., strain gauge) mounted within the rotating drum (both type of energy values hereinafter designated "E") at given constant mixer drum speed values (speed being hereinafter designated "V") which can be plotted graphically as a relationship from which concrete slump ("S") or other rheology value can be calculated. Slump ("S") will be understood to be used interchangeably with other rheology concepts such as slump flow, yield stress, workability, and the like which are capable of being monitored using processor-controlled systems on concrete mixer trucks. Accordingly, the concepts "jump speed data" and "jump speed curve data" can be used herein to refer to the "E/V/S" relationship useful for characterizing the rheology of concrete mixes.

While the use of jumps in mixer drum speed (sudden changes) have been used in the past to measure rheological properties of concrete (e.g., U.S. Pat. No. 8,764,272 of Hazrati et al., owned by Verifi LLC of Cambridge, MA), including the slump of concrete (e.g., WO 2013/144528 A1 of Lafarge), also as mentioned in Cooley et al. as just discussed in the background section, the prior use of jump speed data has been limited in commercial applicability. This is because real-time measurement involving two or more different drum speeds requires large amounts of time. A change in speed from below 6 RPM (e.g., 1-3 RPM) to 8, 10, 15, 18, and 20 RPM or more, and then back to below 6 RPM does not happen frequently during delivery operations.

While it is discussed in ASTM C94 (and Cooley et al.) that high "mixing" speed is used after batching components together, the mixer drum is slowed to "agitation" speed (e.g., 2-3 RPM) for transit purposes. This reduces the risk of having concrete spill out of the truck or causing it to tip over. Thus, high speed jumps do not normally occur during transit, and hence it is believed that the present invention provides a surprisingly novel and inventive approach.

The present inventors realized that they could obtain jump speed data curves from previous concrete deliveries and that these contain data associated with the energy values (pressure or force) associated with rotating concrete (including higher and very high drum speed ranges), the drum speed, and calculated slump (e.g., as might be calculated using data curves at low speed or using pre-established mathematical relationships), could be used preferentially for determining whether it is possible for the monitoring system to calibrate the processor-controlled concrete monitoring system such that slump or other rheology of the current concrete can be monitored at the higher and highest mixing speeds (e.g., 6-20 RPM range).

Accordingly, preferred embodiments of the present invention advantageously incorporate what hitherto is considered an inconvenient, nuisance practice under ASTM C94. This practice involves truck operators rotating the drum at a minimum of 30 revolutions if fluid was dosed at any time before the concrete is poured. The present inventors realized that the concrete is most likely, in these pre-pour drum jump speed events, to be in a state of "equilibrium" and that it was important for the concrete to be in an equilibrium state for the theory of slump continuity to be applied. A state of equilibrium can be confirmed, for example, by measuring the energy (e.g., pressure or force) associated with rotating the mixer drum at constant speed, and confirming that the average energy value over two or more successive drum rotations does not vary (e.g., by plus or minus 5% or 10%) from one rotation to the next. Alternatively, equilibrium can be confirmed by measuring the energy (e.g. pressure or force) associated with rotating the mixer drum at constant speed, and confirming that the instantaneous energy value at an initial point in time does not vary (e.g. by plus or minus 5% or 10%) from the instantaneous energy value at a point one revolution from the initial point.

Hence, an exemplary method of the present invention for concrete monitoring calibration using a processor-controlled system and a delivery mixer truck mixer drum (which rotates at a non-vertical angle with respect to the ground), comprises:

(A) monitoring concrete provided in the mixer drum by measuring, while the concrete is in a state of equilibrium, the energy ("E1") associated with rotating the concrete at a first constant speed ("V1") and energy ("E2") associated with rotating the concrete at a second constant speed ("V2") after a speed jump of plus or minus at least 2.5 rotations per minute (RPM);

(B) calculating a slump value ("S") for the provided concrete based on E1, V1, E2, and V2;

(C) comparing E1, V1, E2, V2, and S as calculated from step (B) with at least two data curves stored in processor-accessible memory, the stored data curves defining an E/V/S relationship for purposes of calculating slump across drum speed ranges of 0.5 RPM-6 RPM and 6 RPM-20 RPM, the at least two stored data curves comprising data obtained from previous deliveries of concrete when the previous concrete was in a state of equilibrium and comprising energy (E) values measured before and after at least 2.5 RPM jumps in constant drum speed (V) and slump values(S) as calculated from the previously stored E and V data, whereby the process-controlled system determines whether any of the at least two stored data curves match the E1, V1, E2, V2, and S values of the provided concrete; and (D) monitoring the slump of the provided concrete in the mixer drum by calculating slump through measurement of the energy associated with rotating the concrete
  (i) within 0.5 RPM-6 RPM and within 6 RPM-20 RPM drum speed ranges, based on one of the at least two stored data curves which is determined to constitute a match in step (C), and providing a visual indication that slump is being calculated by the system for drum speeds higher than 6 RPM: or
  (ii) within the 0.5 RPM-6 RPM range only, if none of the stored curve data is determined to constitute a match in Step (C), and initiating an alert to a system operator or the truck driver, or dispatch center, that the system is active only for monitoring at drum speeds below 6 RPM.

In another embodiment of the present invention, the stored at least two data curves in step (C) are obtained from different previous concrete deliveries.

More preferably, the stored at least two data curves in step (C) comprise mixer drum data of jumps in rotation speed occurring after arrival of the delivery truck at the construction site and before the concrete is poured into place at the delivery site.

Most preferably, at least 50% of the data used for establishing the stored at least two data curves comprises jump speed data obtained at the delivery construction site but before the concrete is poured into place at the site.

Further advantages and features of the present invention are described in detail hereinafter.

BRIEF DESCRIPTION OF DRAWINGS

An appreciation of the benefits and features of the invention may be more readily comprehended through consideration of the written description of preferred embodiments in conjunction with the drawings, wherein.

DETAILED DESCRIPTION OF PREFERRED EMBODIMENTS

Figure 1:
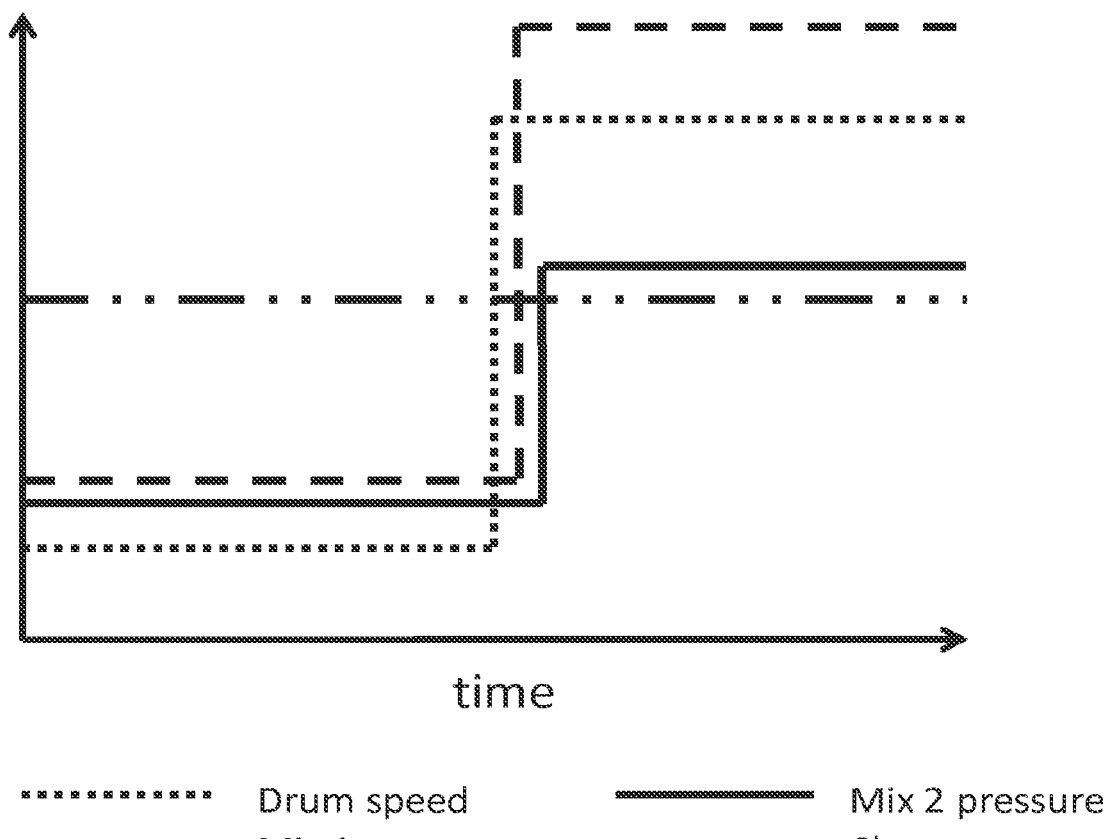
FIG. 1 is a graphic illustration of the "theory of slump continuity" by which the slump of a concrete mix is presumed to be constant before and after a change in the mixer drum rotation speed and the unexpected discovery of the present inventors that two different concrete mix designs can have enormous variability after the drum speed change.

The present invention now will be described more fully hereinafter with reference to the accompanying drawings, in which various exemplary embodiments are shown illustrating variations within the scope of the invention. This disclosure may, however, be embodied in many different forms and should not be construed as limited to the embodiments set forth herein: rather, these embodiments are provided so that this disclosure will be thorough and complete and fully convey the scope of the invention to those of ordinary skill in the art.

The term "concrete" refers to cement (which often contains pozzolanic material such as limestone, fly ash, granulated blast furnace slag) and aggregates (e.g., sand, gravel) and optionally one or more chemical admixtures (e.g., plasticizers for increasing workability, set accelerator, set retarder, air entrainer, air detrainer, plastic shrinkage reducing admixtures, corrosion inhibitors (for rebar), or other admixtures for modifying a property of the concrete, whether in its plastic or hardened state.

While automated concrete monitoring systems are known for monitoring slump, it will be understood that the present invention is applicable during the monitoring of other rheology parameters, including slump, slump flow, yield stress, viscosity, and other rheological parameters. The term "slump" is used in the present specification to illustrate conveniently any of these rheology parameters; and it should be understood that the present invention covers the monitoring of other rheology parameters even when "slump" is indicated.

The present invention sets forth a concrete monitoring calibration method for automated slump monitoring devices in near real-time across different concrete mixer drum rotation speeds and concrete mix designs in a manner that significantly reduces the number of manual slump tests required without sacrificing accuracy.

The processes of the invention may be implemented using automated concrete monitoring systems available from Verifi LLC of Cambridge, Massachusetts, USA, which are based presently on hydraulic pressure sensing and drum speed sensing. The Verifi® technology is variously described in the patent literature (See e.g., U.S. Pat. Nos. 8,764,272, 8,311,678, 8,118,473, 8,020,431, 8,746,954, 8,989,905, 8,727,604, 8,491,717, 8,764,273, among others).

The present inventors also believe that the present invention could be implemented using force (or stress/strain gauge type) sensors available from Sensocrete (e.g., U.S. Publ. No. 2015/0051737 A1 of Berman) or IBB Rheology (e.g., U.S. Publ. No. 2012/0204625 A1 of Beaupre et al), both of Montreal, Canada.

Thus, the concept of energy ("E") measurement refers to an exemplary use of one or more pressure sensors for measuring the hydraulic pressure associated with rotating concrete in a truck-mounted concrete mixer drum, or, alternatively, to a force probe mounted upon an inner wall or blade of the mixer drum which emits an electrical signal corresponding to the stress exerted on the probe as it moves through concrete within the rotating drum.

It is preferred that the truck-mounted mixer drum used in combination with the automated monitoring system should have, at a minimum, at least two mixing blades spirally mounted on an inner wall of the drum which is rotatable about a non-vertical axis (e.g., at an angle with respect to level ground) and an ability to mix a volume between 0-15 cubic yards of concrete within the mixer drum. The truck should preferably have a drive means for rotating the mixer drum containing the provided concrete at a constant speed in the range of 0.5-20 RPM, one or more data memory storage locations, and one or more computer processor units for monitoring the rheology of the concrete.

The rotation speed of the mixer drum can be measured preferably using one or more of accelerometer, magnets, or rotary encoders mounted on the mixer drum, such as by using an annular arrangement of magnets passing field effect sensors, or other known means which provide an output signal to the system processor, such as Eaton sensors. An exemplary speed sensing device is a gyroscopic rotational monitoring system taught in International Publication No. WO 2015/073825A1 of Richard Jordan et al., owned by Verifi LLC.

Additionally, it is preferred that the concrete delivery truck have one or more systems for introducing water, chemical admixture, or other fluid into the concrete to adjust rheology, and that the delivery system be controlled by a processor unit in connection with the monitoring or control of concrete provided in the truck-mounted mixer drum.

Typical concrete delivery trucks allow the driver to make a speed jump (or sudden change) in the mixer drum rotational speed simply by manipulating a dial, lever, button, or other switch control within the truck cab.

A "speed jump" is illustrated as a step in FIG. 1. While the slump of the concrete remains the same before and after the change in mixer drum speed (according to the "theory of slump continuity," it is the drum speed and not the concrete that changes suddenly), it was an important discovery for the present inventors to realize that the energy value as sensed by automated concrete monitoring systems becomes unpredictable at higher mixing speeds (e.g., 6-20 RPM or more); and, moreover, that the non-linear behavior between the derived energy/force value cannot be made "linear" by a simple multiplication factor, as previously espoused by Cooley et al (as discussed in the background section).

FIG. 1 further illustrates dramatic unpredictability due to high speed mixing variability, a surprising characteristic discovered by the present inventors when examining two different concrete mix designs, both of which are presumed, according to the theory of slump continuity, to have the same constant slump value (shown by horizontal line) before and after a change in the mixer drum speed. As shown in FIG. 1, the monitored energy (E) associated with rotating two different concrete mix loads, Mix 1 and Mix 2, within a truck-mounted mixer drum, is plotted as a function of time. At the lower drum speed, the pressure value corresponding to the energy required to rotate the drum for Mix 1 and Mix 2 appears similar, as their respective energy data curves nearly coincide and overlap. However, after the sudden increase in drum speed, the sensed energy associated with rotating each of Mix 1 and Mix 2 are surprisingly different, and spaced much further apart, as compared to the curve behavior seen before the drum speed jump. The disproportionately large affect on the sensed energy on the energy/speed/slump relationship is believed by the present inventors to be due to a change in the nature and content of the aggregates, and to some extent the nature of cement in different concrete mix designs, among other concrete mix design factors (See e.g. Tattersall 1991).

The present inventors believe that it is important for the concrete mix to be monitored while in a non-segregated state. By "non-segregated," it is meant that the concrete is uniformly mixed so that the aggregates (e.g., sand, crushed stone) are not unevenly dispersed within the mix volume. It is also important for that the concrete mix not be dosed with a fluid (e.g., water, chemical admixture) in the moments before, during, or after the speed change or jump which is being monitored.

The concept of speed change monitoring is premised upon the present inventors' understanding that the concrete mix should be in a state of equilibrium. In other words, the mixer drum is rotated at a constant first speed for a period of time, resulting in an equilibrium output in terms of the energy required to move the concrete. After equilibrium is achieved, the drum rotation speed is changed to another speed (above or below), preferably more than one (1) RPM difference (and more preferably at least 2.5 RPM or more difference) and held at the second speed until equilibrium is again obtained. By "equilibrium," it is meant that the initial value of the output in terms of energy associated with rotation of the concrete load in the drum at a given speed does not significantly vary or differ from the output at the end of the drum revolution (e.g., beyond a pre-established or pre-selected error margin or threshold value, such as 3%, 3.5%, 4%, 4.5%, 5%, etc., which can be selected by the system programmer, manager, or user based on various factors such as sensor accuracy, mixer drum design, mixer drum drive mechanism, and others). Or described another way: the concept of "equilibrium" refers to the average output in terms of energy, if represented as a periodic wave on a video monitor, wherein the average energy value should not differ significantly between successive drum rotations (e.g., beyond a pre-established or pre-selected error margin or threshold value, as discussed above).

It is also preferred for purposes of achieving the most accurate monitoring and measurements in the present invention that the concrete build-up (e.g., concrete hardened on portion of the drum wall or blades, such as from previous deliveries) is less than one cubic yard.

Figure 2:
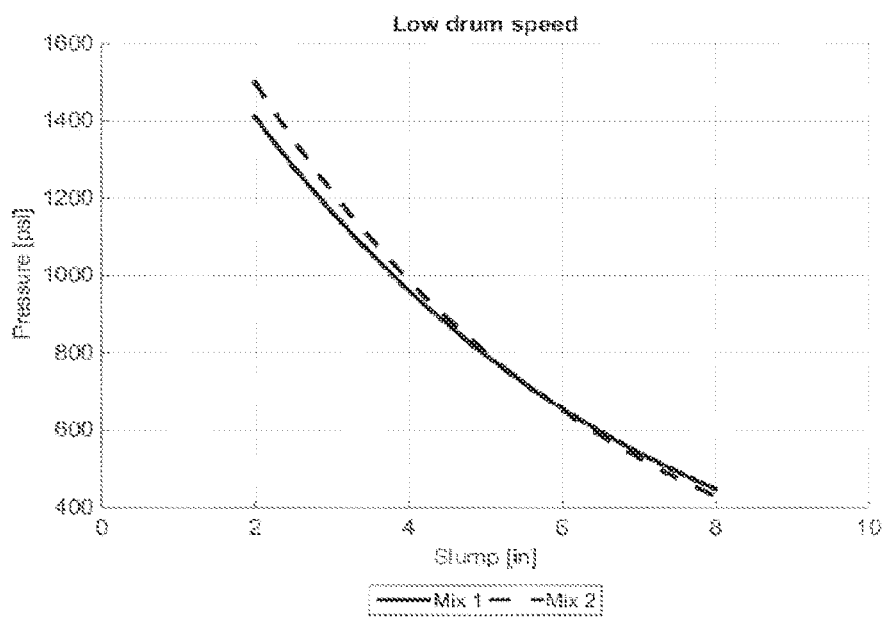
FIGS. 2 and 3 are graphic illustrations of the slump behavior of two different concrete mix designs at, respectively, low mixing speed (i.e., 3 RPM as shown in FIG. 2) and at high mixing speed (i.e., 18 RPM as shown in FIG. 3) which was noted by the present inventors to show variability only at high drum mixer speed but not at low drum mixer speed.
Figure 3:
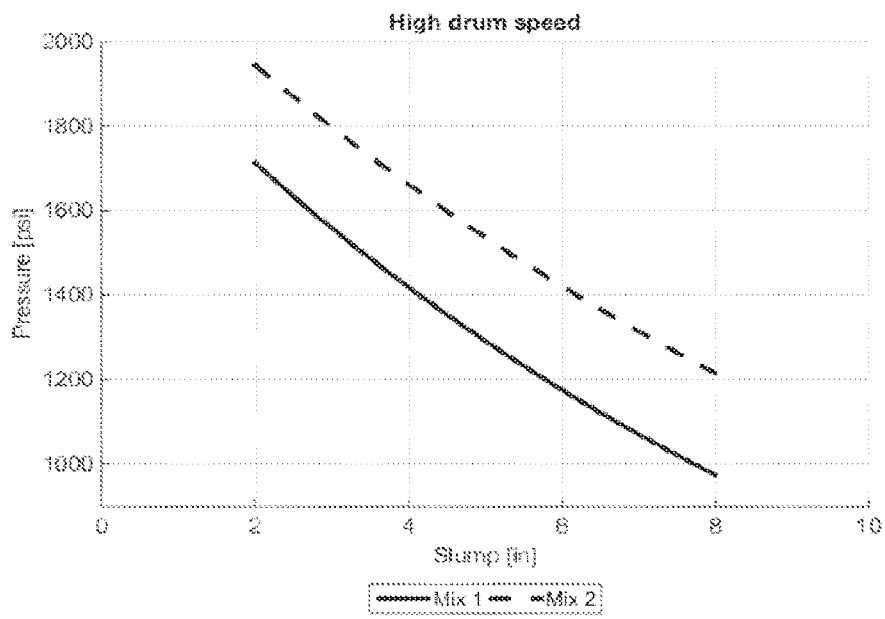

FIGS. 2 and 3 illustrate the slump behavior of two different concrete mix designs at different mixer drum speeds. In particular, FIG. 2 illustrates slump behavior of the two different concrete mixes at the relatively low speed of 3 RPM. At such low agitation speeds which are typical of delivery trucks during transit, the slump behavior of different concrete mix designs is similar in that the curve data is similar (for energy (E)/speed (V)/slump(S) relationship). In contrast, FIG. 3 illustrates that at high mixing speed (e.g., 18 RPM, but the present inventors believe that the curves would be similar for 12-20 RPM) the relationship between energy and slump values are substantially different. Here the energy is shown to differ by more than 200 pounds per square inch (psi). This difference in the energies associated with rotating two different concrete mix designs is much more pronounced at higher drum speeds, as compared to lower speeds (3 RPM) at which the difference was no more than 100 psi at any given point over the entire slump range from 2 to 8 inches.

From these surprising results, the present inventors realized that when viewing collected E/V/S data curves for different concrete mix designs at low and high mixing speeds, there was a long felt and desperate need for the ability of the present invention to achieve slump monitoring calibration at the higher (6-12 RPM) and highest (12-20 RPM) drum speeds, thus achieving an ability for each delivery truck to perform wide speed range monitoring, without having to perform testing (manual slump cone) for each mix design.

Thus, exemplary method of the present invention for concrete monitoring calibration using a processor-controlled system and a delivery mixer truck mixer drum, comprises:
(A) monitoring concrete provided in the mixer drum by measuring, while the concrete is in a state of equilibrium, the energy ("E1") associated with rotating the concrete at a first constant speed ("V1") and energy ("E2") associated with rotating the concrete at a second constant speed ("V2") after a speed jump of plus or minus at least 2.5 rotations per minute (RPM);
(B) calculating a slump value ("S") for the provided concrete based on E1, V1, E2, and V2;
(C) comparing E1, V1, E2, V2, and S as calculated from step (B) with at least two data curves stored in processor-accessible memory, the stored data curves defining an E/V/S relationship for purposes of calculating slump across drum speed ranges of 0.5 RPM-6 RPM and 6 RPM-20 RPM, the at least two stored data curves comprising data obtained from previous deliveries of concrete when the previous concrete was in a state of equilibrium and comprising energy (E) values measured before and after at least 2.5 RPM jumps in constant drum speed (V) and slump values(S) as calculated from the previously stored E and V data, whereby the process-controlled system determines whether any of the at least two stored data curves match the E1, V1, E2, V2, and S values of the provided concrete; and
(D) monitoring the slump of the provided concrete in the mixer drum by calculating slump through measurement of the energy associated with rotating the concrete
  (i) within 0.5 RPM-6 RPM and within 6 RPM-20 RPM drum speed ranges, based on one of the at least two stored data curves which is determined to constitute a match in step (C), and providing a visual indication that slump is being calculated by the system for drum speeds higher than 6 RPM: or
  (ii) within the 0.5 RPM-6 RPM range only, if none of the stored curve data is determined to constitute a match in Step (C), and initiating an alert to a system operator or the truck driver, or dispatch center, that the system is active only for monitoring at drum speeds below 6 RPM.

In further exemplary methods of the present invention, the equilibrium state of the concrete is confirmed by averaging the energy associated with rotating concrete in the mixer drum at constant speed through each of at least two successive drum rotations and determining that the average energy value does not vary over the at least two successive drum rotations, beyond a pre-established error margin value (i.e., which could be selected by the programmer): or, alternatively, by confirming that an initial value of energy associated with rotation of the concrete in the drum at a given speed does not differ from the output at the end of a complete drum rotation, beyond a pre-established error margin value.

In other exemplary methods, the mixer drum speed jump in step (A) can be effectuated by an operator of the concrete delivery truck activating a mixer drum speed switch, dial, lever, or pushbutton (i) to increase mixer drum speed from 0.5-6 RPM to 6-20 RPM or to decrease drum speed from 6-20 RPM to 0.5-6 RPM (wherein the increase or decrease is by at least 2.5 RPM): or (ii) to change drum speed by at least 2.5 RPM between two mixer drum speeds within the range of 4.5-20 RPM.

In further exemplary methods, the slump(S) in step (B) can be calculated using any known methods, such as (i) by rotating the provided concrete in step (A) at a drum speed whereby S1 or S2 is within the range of 0.5-6 RPM, and employing at least one stored data curve defining an E/V/S relationship wherein the speed (V) is below 6 RPM or (ii) in establishing a linear relationship for E1, V2, E2, and V3, which, if plotted as a function of drum speed (V) along a horizontal axis against energy (E) along a vertical axis, whereby the slope value of the line established by (E1, V1) and (E2, V2) and intercept value of the line which intercepts the horizontal axis ($E_0$ at V=0)) are compared to a pre-established linear relationship of slope/intercept/slump(S) values as previously stored in controller-accessible memory. The method in (i) can be used for jump speeds between low RPM drum speeds (0.5-6 RPM) and higher drum speeds (6 RPM to 20 RPM or even higher); whereas the method in (ii) does not necessarily require jump speeds involving lower drum speeds (below 6 RPM, such as 3-4 RPM). In the slope/intercept method (ii) mentioned above, the system process can be programmed using a linear equation based on E1, V1 and E2, V2 whereby slump(S) of provided concrete in step (A) can be predicted by using a pre-stored mathematical equation. The equation which reflects E/V/S relationship might be formulated by the system programmer, for example, based on regression analysis or using a least-squares approach to jump speed data obtained from previously sampled concrete mixes.

Thus, in exemplary methods of the invention, the slump calculation of the provided concrete in step (B) involves a change of speed involving mixer drum speed into or out of the range of 0.5 RPM-3.5 RPM, such that a low speed curve can be used: while in other exemplary methods of the invention, it may not be necessary to use low drum speeds (<6 RPM), but the aforementioned slope/intercept method can be used to calculate slump(S) using a pre-stored equation as desired by the monitoring system programmer or architect. The linear equation can be based, for example, on a regression analysis using the concrete customer's concrete mix designs and other factors such as the design or type of the truck or mixing drum.

In still further exemplary embodiments, the values E1, V1, E2, and V2 as measured in step (A) are stored into memory. For example, the E1, V1, E2, V2, and calculated slump(S) values can be stored into the same memory location of previously stored E/V/S curves if found to match, in order to improve the resolution or accuracy of the data curves. If a ticket is assigned to the concrete batch load, the measured E1, V1, E2, V2, and S values can be compared with any data curves previously stored in memory (library), and the monitoring system processor can be programmed to confirm that the ticketed batch conforms to at least one of the pre-stored E/V/S curve data relationships. The system processor can also be programmed to send visual confirmation to a system operator or user that the provided concrete conforms to the batch information (e.g., concrete mix identification) on the ticket.

Thus, in still further exemplary embodiments, the E1, V1, E2, and V2 values (along with any calculated slump(S) values) can be included in the previously stored curve data, such as the at least two data curves mentioned for step (C).

Once the slump of the provided concrete in step (A) is calculated in step (B), using any known method, the present invention then involves comparing the slump, in step (C), to at least two stored data curves (and more preferably to at least six data curves) defining E/V/S relationships for calculating slump across drum speed ranges of 0.5 RPM-6 RPM and 6 RPM-20 RPM. The stored data is preferably obtained from previously deliveries involving (i) mixer drums on different concrete delivery trucks: (ii) mixer drum speed jumps occurring at the delivery site before the concrete is poured into place at the site: or (iii) both (i) and (ii). More preferably, in step (C), the at least two stored data curves defining an E/V/S relationship for calculating slump across the drum speed ranges of 0.5 RPM-6 RPM and 6 RPM-20 RPM, comprise data based on mixer drum speed jumps occurring at the delivery site before the concrete is poured. And, most preferably, in step (C), the processor-accessible memory comprises at least six stored data curves define E/V/S relationships for calculating slump across the drum speed ranges of 0.5 RPM-6 RPM and 6 RPM-20 RPM; and the data of said at least six stored data curves comprise at least 50 percent of drum speed jumps occurring at the delivery site before the concrete is poured.

The at least two stored data curves which define E/V/S relationships for calculating slump across the drum speed ranges of 0.5 RPM-6 RPM and 6 RPM-20 RPM may be located in memory off of the delivery truck, such as at a dispatch center, a central office, or in the cloud. In preferred methods of the invention, a "library" of stored data curves can be downloaded from a central memory location, such as from the cloud, to controller-accessible memory on the truck (e.g., memory connected to the truck-based slump monitoring system). Hence, a library of pre-stored data curves defining E/V/S relationships for calculating slump across the drum speed ranges of 0.5 RPM-6 RPM and 6 RPM-20 RPM, can be periodically updated into each truck within a fleet, even as the various fleet trucks upload their E1, V1, E2, V2, and corresponding (calculated) slump data based on provided concretes (see Step (A)) for each delivery operation.

In still further exemplary methods, the measured energy (E) is measured using at least one hydraulic pressure sensor effective for measuring the pressure associated with rotating the provided concrete in the mixer drum, or, as previously discussed, can also be measured using a force sensor or stress gauge, mounted on the inner wall of the rotating mixer drum, as the sensor/gauge moves through the concrete being rotated in the rotated mixer drum (whereby the concrete exerts greater force on the probe as its workability decreases).

Fortunately, it is somewhat less complex when it comes to using different sensor types for monitoring during drum speed jumps. Thus, exemplary methods of the invention may employ at least one drum-mounted accelerometer, magnet, or rotary encoder for measuring drum speeds.

The methods of the present invention may be used to confirm that the rheology of the provided concrete loaded into the mixing drum conforms to the rheology behavior accordance with the batch information contained on "tickets" (paper or electronic) which is issued by the batch plant. (If the ticket is in electronic form, the batch information is downloaded into a memory location of the slump monitoring system). Accordingly, exemplary methods of the present invention further comprise: entering into controller-accessible memory the ticket batch information corresponding to the provided concrete in step (A): determining whether any of the stored at least two data curves defining E/V/S relationships for calculating slump across the drum speed ranges of 0.5 RPM-6 RPM and 6 RPM-20 RPM in step (C) are pre-assigned to the entered ticket batch information; and verifying by performing steps (C) and (D) (i) to monitor the provided concrete and to confirm that the provided concrete conforms to a data curve pre-assigned to the entered ticket batch information.

If the provided concrete does not conform to the data curve pre-assigned to the entered ticket batch information, then the system is programmed (see step (C)) to determine whether another stored data curve in processor-accessible memory matches the provided concrete. In other words, if the processor-controlled slump monitoring system does not find a matching data curve in its on-board library, then, in exemplary embodiments of the invention, the system processor can search for or retrieve a matching data curve that could be located in a remote location, such as a library of E/V/S data curves stored in the cloud, or at a remote serve location such as at the offices of the monitoring system operator or programmer, or other location.

In still further exemplary embodiments, assuming that slump of a provided concrete in step (A) is monitored before and after a speed jump, the slump of the provided concrete can be adjusting by introducing an amount of water, chemical admixture, or mixture thereof, and the amount of material introduced is based on slump calculated using jumps between the drum speed range of 0.5-6 RPM and the drum speed range of 6-20 RPM.

The present inventors further note that, if a matching stored data curve is found in step (D) (i), the system processor can be programmed to add E1, V1, E2, and V2 data as obtained in step (A), as well as the calculated slump(S) value into the matching curve data. An alert can be sent to the operator or user of the concrete monitoring system that the new data has been included in the stored curve data.

The present invention provides a concrete monitoring system configured to perform steps (A) through (D) as well as any, some, or all of the above-described exemplary methods.

It may be also fair to say that the present invention provides a way for a community of concrete monitoring systems, installed on a fleet of delivery trucks, to contribute to the improvement and/or enhancement of individual monitoring system performance. This is done by allowing for the possibility of increasing the stored library of data curves for defining E/V/S relationships across the entire spectrum of mixer drum rotation speeds (0.5 to 20 RPM or more), as well as increasing the data resolution for individual data curves. In other words, the ability for each individual monitoring system to contribute E1, V1, E2, V2, and calculated S data will enhance the breadth of the data curves library as well as the accuracy of each curve data set.

While the present inventors choose to summarize the jump speed in step (A) to constitute a difference of at least 2.5 RPM (as an increase or decrease in drum speed), the actuality is that during typical concrete delivery operations, different truck drivers will change speeds according to their different habits and/or according to the nature of their trucks or mixing drum equipment. Some drivers may move their speed dial or lever from agitation speed (2-3 RPM) to the highest setting possible (e.g., 20 RPM or more), while others may prefer to jump between 12-20 RPM down to 6-9 RPM due to other considerations, such as the sound or vibration characteristics of the particular truck/drum set up. In either case, the ability of the present invention to contribute the corresponding E1/V1/E2/V2 and S data to the library of stored curve data will serve to bring the E/V/S relationships into sharper focus across the speed ranges of 0.5 RPM-6 RPM and 6 RPM-20 RPM (where minimum jump is at least 2.5 RPM).

Figure 4:
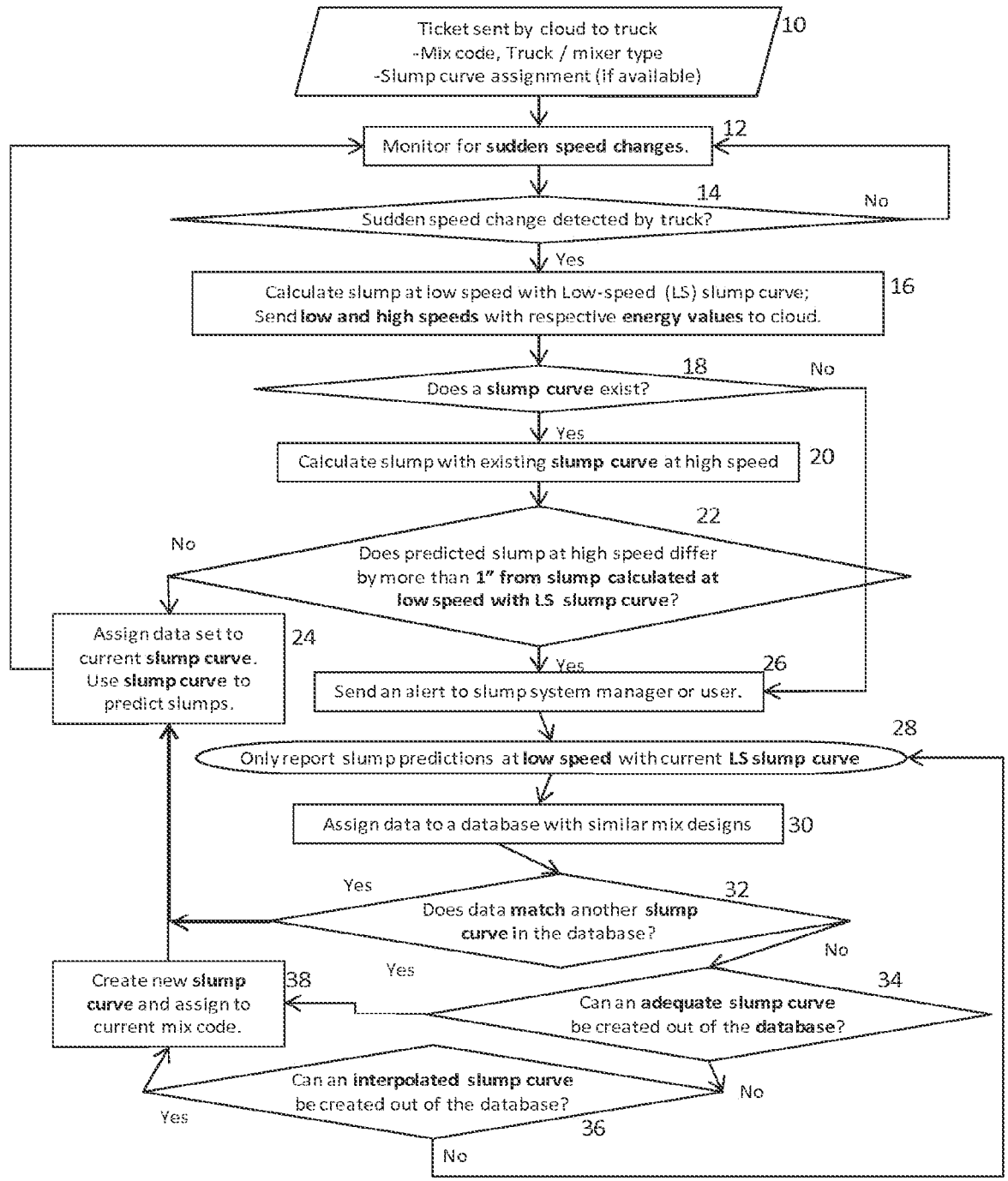
FIG. 4 is a block diagram flow chart to illustrate exemplary processes of the present invention wherein concrete slump data, obtained from automated slump monitoring systems during normal concrete delivery operations, is used to create energy or force/slump/drum-speed relationships for accurate wide speed measurements and slump (or other rheology monitoring and/or adjustment) using automated concrete mix monitoring systems.

FIG. 4 employs a flow chart to illustrate significant stages of an exemplary method of the invention with respect to the concrete delivery operation. At the beginning of the concrete delivery operation designated in the block at 10 in FIG. 4, a set of instructions commonly referred to as a "ticket," an electronically transmitted packet of information that could also be printed onto paper slip, is transmitted from a dispatch center to the delivery truck via communication port and electronic automated slump monitoring system. The ticket typically contains information such as the concrete mix design, the customer identity and delivery location, and preferably other information such as whether a specific slump curve exists (i.e., an existing calibration curve for predicting relationship between energy and correlated slump value at a given drum speed). The commercially available Verifi R Slump Management System provides for this initial calibration information automatically for the convenience of its users. The ticket will usually have truck identification information (as the ticket is sent to the truck by the dispatcher who matches up the truck with the ticket).

In accordance with the present invention, the system processor on the delivery truck is programmed to detect when an abrupt change in mixing speed takes place, as designated at block 12 in FIG. 4. This jump in speed can be, for example, from a low mixing speed range (e.g., between 0.5-6 RPM) to a higher mixing speed (e.g., 6-20 RPM), and, as another example, may be a jump from high to low mixing speed. However, in any event, the difference in the speed change should preferably be at least 2.5 RPMs for purposes of data collection and monitoring using the methods of the present invention. It is noted by the present inventors that these abrupt changes in mix speed within the concrete delivery speed routine occur because it is mandatory for drivers to bring their drum speeds up to what is called "mixing speed" whenever water and/or chemical admixtures are introduced into the concrete load, but the actual "mixing speed" is usually determined by the particular concrete delivery truck manufacturer. For purposes of monitoring and compiling a curve data library in connection with implementing methods of the present invention, regardless of whether a liquid has been added ten drum rotations or two rotations before the sudden change or jump in drum speed, it is important that the concrete be at equilibrium before and after the jump speed event, otherwise the data should not be used or included in the data library for purposes of accomplishing the present invention. (See discussion of "equilibrium" above).

The present inventors believe that the enormous variability in the sensed energy or force values and curves, when concrete is monitored at high drum speeds (>6 RPM and up to 20 RPM or higher) can now be viewed, in a practical sense, to amplify the sensitivity of concrete monitoring systems. The large variability in the sensed energy (or force) at high speeds, previously a cause for potential error in slump monitoring, can now be used for sensitivity in selection of the appropriate data curves derived from historical data compiled in the cloud or elsewhere in a second processor or computer system located at a remote site.

The system processor is programmed to assemble data curves which can be considered to be fairly robust in that different drum speeds can be monitored and values inputted into the system. For example, it is often the case that a given truck driver does not typically change mixer drum speed by turning the speed dial all the way to the top drum speed. Rather, the truck driver may have a personal preference for turning the speed dial to somewhere within 10-15 RPM), or may be influenced by the condition or state of the truck (e.g., the sound made by the rotating mixer drum at a given drum speed might be the factor which motivates the truck driver to set the drum speed at a certain point). Hence, the data curves which reflect the energy or force/rheology/speed correlations made by the system processor will tend to provide a complete curve profile over repeated different concrete deliveries.

It is further noted in FIG. 4 that, if the system processor detects that a jump in drum speed has occurred, as designated by block 14, wherein the change in speed meets or exceeds a limit which is pre-established by the program software (e.g., difference of at least 2.5 RPM as between first and second speed within the given low and high speed mixing ranges), then the data for both low speed and high speed is sent to an off-truck database (e.g., at a remote site or center), such as to the cloud (designated as at block 16). In other words, the data will contain the energy (pressure or force) and drum speed values (at both low and high speed), and this data will be transmitted to another processor for storing into a database (e.g., the cloud).

The monitoring system processor on the truck is also programmed to determine whether a calibration data curve (e.g., a "slump" curve or energy/slump/speed correlation) already exists, designated at block 18 in FIG. 4. If the system processor (18) determines that a slump calibration curve does not exist (e.g., the ticket does not designate an existing slump curve), then the system processor sends an alarm or alert to the system provider, manager, or architect (designated by block 26 in FIG. 4); and the processor only allows the slump system to monitor and adjust the concrete load only at low drum speeds (as designated by block 28) and preferably collects the new data (energy/drum speed) for future use by the system (block 30).

If the system processor detects that a slump curve does exist (for example, as designated in the ticket information) then the system processor is instructed by the software program to calculate slump or other rheology value (as designated at block 20) such that the slump is calculated at both high and low drum speeds.

In further embodiments, the system processor is further programmed, as shown at block 22 in FIG. 4, to confirm whether the existing slump curve preserves slump continuity by comparing the slump predicted at high speed with the existing slump curve to the slump predicted at low speed with the low-speed slump curve. Slump continuity is confirmed when these slump predictions are within a given tolerance. For example, when the drum speed is jumped from 3 RPM to 8 RPM, the slump value predicted at both of these speeds should not differ by more than one (1) inch slump value; and, more preferably, the slump value should not differ by more than one-half (½) inch. The tolerance should be selected by taking into consideration the sensitivity of the rheology measurement system, e.g., the hydraulic pressure sensor or force sensor (stress gauge) employed to measure the energy or forced required to rotate the concrete load at a given drum speed (or the precision of the slump cone test under ASTM C143 if this was used to make the initial calibration curves).

As illustrated by block 24 in FIG. 4, if the system processor confirms that predicted slump at high and low speeds differ by a value that does not exceed a programmed tolerance value (22 in FIG. 4), then the system processor will assign the data (the energy and drum speed values previously sent to the cloud or other system processor-accessible memory location, as designated in block 16) to a database for the given slump curve, so that the truck-mounted system processor, relative to the current or to subsequent concrete deliveries, can use the data as or as part of established slump curve data. The data can be used, for example, when the system processor monitors the jump speed data (as designated in block 12).

If the system processor confirms that the predicted slumps at high and low speeds differ by a value that does exceed a programmed tolerance value (as designated in block 22 of FIG. 4), then the system processor is programmed to send an alarm or alert to the slump monitoring system operator ("Verifi" LLC shown as example in FIG. 4) or to another designated recipient, such as a quality control manager, or other designated recipient (as designated at block 26).

Once an alarm or alert is sent to the slump monitoring system operator or other designated recipient or recipients (block 26), if an existing slump curve is not detected (block 18) or the new data is determined to exceed a given tolerance value (block 22), then the slump monitoring system is preferably programmed to search existing calibration curves (block 32) and/or to evaluate the data (block 30) obtained from prior deliveries to ascertain whether a calibration curve can be generated (block 36) or appropriated for use in high speed mixing ranges in the present delivery and assigned to the current mix design (block 38) or perhaps used for future deliveries (see e.g., block 24) and future monitoring and collection of jump speed data (blocks 12-20 and following again through flow diagram).

The present invention is described herein using illustrative examples and scenarios, and variations of the present invention might now appear practical, in light of these illustrations and descriptions, to those versed in the use of automated concrete monitoring systems. The exemplary embodiments described above have been based on using sudden speed change data and establishing a slump relationship based on energy (e.g., hydraulic pressure) or force (stress gauge) data, slump, and drum speed. Slump is thus understood as a function of the pressure and drum speed. In other exemplary embodiments, which are also based on the same assumption that the slump of the concrete stays the same throughout a given jump speed event, the rheology may be characterized or calculated using a different method whereby one plots the pressure (vertical-axis on a graph) against drum rotation speed (horizontal-axis), such that, as drum speed increases, the pressure typically increase. Hence, for a given jump speed event, one can draw a line through the two data points (for pressure), and define the slump relationship as a function of the slope of the line and intercept with the vertical-axis (e.g., Slump=Function (Slope, Intercept). The slopes and intercepts can then be used as an alternative way to group the data corresponding to different mix designs whereby it is stored, sorted, or retrieved by the slump system processor or cloud based system).

Again, the present invention is described herein using a limited number of illustrative embodiments not intended to limit the scope of the invention as otherwise described and claimed herein.

What is claimed is:

1. A concrete delivery operation comprising:
   transmitting electronically from a dispatch center to a delivery truck having a mixing drum an electronically transmitted packet of information that comprises information of a concrete mix design, a customer identity and a delivery location;
   detecting when an abrupt change meeting or exceeding a pre-established limit in mixing speed of said mixing drum takes place on the delivery truck;
   if it is detected that said abrupt change in mixing speed has occurred, then new data for both a low mixing speed and a high mixing speed is sent to an off-truck database;
   collecting the new data; and
   assigning the new data to the current mix design.

2. The concrete delivery operation of claim 1, wherein said abrupt change is at least 2.5 RPM.

3. The concrete delivery operation of claim 1, wherein said mixing speed is measured with at least one drum-mounted accelerometer, magnet or rotary encoder.

4. The concrete delivery operation of claim 1, wherein said new data comprises hydraulic pressure necessary to rotate said mixing drum.

5. The concrete delivery operation of claim 4, wherein said hydraulic pressure is measured by one or more pressure sensors associated with rotating concrete in said mixing drum.

6. The concrete delivery system of claim 4, wherein said hydraulic pressure is measured with a force probe mounted in said mixing drum which emits an electrical signal corresponding to stress exerted on said force probe as it moves through concrete within said mixing drum.

7. The concrete delivery operation of claim 1, wherein said low mixing speed is in a range of between 0.5 and 6 RPM.

8. The concrete delivery operation of claim 1, wherein said transmitted packet of information further contains information on whether a calibration curve for predicting the relationship between energy and correlated slump valve at a given drum speed exists.

* * * * *